(12) United States Patent
Sbrizzi et al.

(10) Patent No.: US 11,754,654 B2
(45) Date of Patent: Sep. 12, 2023

(54) METHOD AND DEVICE FOR DETERMINING A MOTION FIELD FROM K-SPACE DATA

(71) Applicant: KONINKLIJKE PHILIPS N.V., Eindhoven (NL)

(72) Inventors: Allessandro Sbrizzi, Ultrecht (NL); Cornelis Antonius Theodorus Van Den Berg, Ultrecht (NL)

(73) Assignee: Koninklijke Philips N.V., Eindhoven (NL)

( * ) Notice: Subject to any disclaimer, the term of this patent is extended or adjusted under 35 U.S.C. 154(b) by 671 days.

(21) Appl. No.: 16/622,371

(22) PCT Filed: Jun. 20, 2018

(86) PCT No.: PCT/EP2018/066342
§ 371 (c)(1),
(2) Date: Dec. 13, 2019

(87) PCT Pub. No.: WO2019/002034
PCT Pub. Date: Jan. 3, 2019

(65) Prior Publication Data
US 2020/0142018 A1 May 7, 2020

(30) Foreign Application Priority Data
Jun. 27, 2017 (EP) .................................. 17178117

(51) Int. Cl.
*G01R 33/563* (2006.01)
*G06T 7/269* (2017.01)
(Continued)

(52) U.S. Cl.
CPC ......... *G01R 33/56308* (2013.01); *A61N 2/02* (2013.01); *G01R 33/4808* (2013.01);
(Continued)

(58) Field of Classification Search
CPC .......... G01R 33/56509; G01R 33/4808; G01R 33/56308
See application file for complete search history.

(56) References Cited

U.S. PATENT DOCUMENTS 5,262,725 A * 11/1993 Cuppen ................ G01R 33/565
324/309
6,236,738 B1 * 5/2001 Zhu ........................ G06T 7/215
382/107
(Continued)

FOREIGN PATENT DOCUMENTS

JP 2009160378 A1 7/2009

OTHER PUBLICATIONS

Harris et al "Ultrafast Volumetric Cine MRI (VC-MRI)" Proceedings of the International Society for Magnetic Resonance in Med. ISMRM No. 3210 (2016).
(Continued)

*Primary Examiner* — Dixomara Vargas

(57) ABSTRACT

The invention relates to a motion determination device for determining the motion of an object. The motion determination device comprises a magnetic resonance (MR) information providing unit (2, 5) for providing an MR image of the object (6) and for providing non-image MR data of the object which have been acquired at different acquisition times, and a motion determination unit (9) for determining a motion field, which describes the motion of the object (6), depending on the provided non-image MR data acquired at the different acquisition times and the provided MR image. Since the non-image MR data, which are preferentially k-space data, are directly used for determining the motion field, i.e. without an intermediate reconstruction of MR images based on the non-image MR data, the motion field can be determined with a very high temporal resolution.

20 Claims, 9 Drawing Sheets

(51) Int. Cl.
*A61N 2/02* (2006.01)
*G01R 33/48* (2006.01)
*G01R 33/565* (2006.01)

(52) U.S. Cl.
CPC ........ *G01R 33/56509* (2013.01); *G06T 7/269* (2017.01); *G06T 2207/10016* (2013.01); *G06T 2207/10088* (2013.01)

(56) References Cited

U.S. PATENT DOCUMENTS

| | | | |
|---|---|---|---|
| 6,950,542 | B2 | 9/2005 | Roesch et al. |
| 8,417,007 | B2 * | 4/2013 | Yui ................. G01R 33/56308 |
| | | | 382/131 |
| 8,825,138 | B2 | 9/2014 | Mistretta |
| 10,045,754 | B2 * | 8/2018 | Klinder ................. G06T 3/4038 |
| 10,342,558 | B2 | 7/2019 | Steckner et al. |
| 2006/0182349 | A1 | 8/2006 | Valdez |
| 2006/0224363 | A1 | 10/2006 | Valdez |
| 2006/0226836 | A1 | 10/2006 | Shu et al. |
| 2010/0142778 | A1 | 6/2010 | Zhuo et al. |
| 2012/0155727 | A1 * | 6/2012 | Orderud ................. G06T 7/262 |
| | | | 382/154 |
| 2013/0108117 | A1 | 5/2013 | Kabus et al. |
| 2013/0131492 | A1 | 5/2013 | Saranathan et al. |
| 2014/0219531 | A1 | 8/2014 | Epstein et al. |
| 2014/0254898 | A1 | 9/2014 | Wang et al. |
| 2014/0296698 | A1 | 10/2014 | Bauer et al. |
| 2014/0357980 | A1 * | 12/2014 | Hayes ................. A61B 6/5264 |
| | | | 600/411 |
| 2016/0073993 | A1 * | 3/2016 | Ouyang ................. A61B 6/527 |
| | | | 600/411 |
| 2016/0095565 | A1 * | 4/2016 | Fenchel ................. A61B 5/113 |
| | | | 600/408 |
| 2017/0082718 | A1 | 3/2017 | Beck |
| 2017/0160366 | A1 * | 6/2017 | Tisdale .............. G01R 33/5613 |
| 2017/0249735 | A1 * | 8/2017 | Feng ....................... G06V 10/42 |
| 2021/0158543 | A1 * | 5/2021 | Sun ....................... G06N 3/0454 |
| 2021/0311152 | A1 * | 10/2021 | Hu ................... G01R 33/56509 |
| 2022/0047227 | A1 * | 2/2022 | Heukensfeldt Jansen ................... A61B 6/5264 |
| 2022/0101537 | A1 * | 3/2022 | Sun ....................... G06T 3/4053 |

OTHER PUBLICATIONS

Atkinson et al "Automatic Correction of Motion Artifacts in Magnetic Resonance Images Using an Entropy Focus Criterion" IEEE Transactions of Medical Imaging, vol. 16, p. 903-910 (1997).
Barry et al "Hybrid Two-Dimensional Navigator Correction; A New Technique to Suppress Respiratory Induced Physiological Noise in Multi-Shot Echo Planar Function MRI" Neuroimage, vol. 39, p. 1142-1150 (2008).
Van der Kouwe et al. "Real Time Rigid Body Motion Correction and Shimming Using a Cloverleaf Navigators" Magnetic Resonance in Med. 56(5) p. 1019-32 (2006).
Search Report and Written Opinion from PCT/EP2018/066342 dated Oct. 12, 2018.
Liang et al.: "Motion-Compensated Keyhole /RIGR Imaging", Proceedings of the International Society for Magnetic Resonance in Medicine, ISMRM, 8th Scientific Meeting and Exhibition, Philadelphia, PA, USA, Apr. 1-7, 2000,XP040581884.

* cited by examiner

METHOD AND DEVICE FOR DETERMINING A MOTION FIELD FROM K-SPACE DATA

CROSS REFERENCE TO RELATED APPLICATIONS

This application is a U.S. national phase application of International Application No. PCT/EP2018/066342 filed on Jun. 20, 2018, which claims the benefit of EP Application Serial No. 17178117.2 filed on Jun. 27, 2017 and is incorporated herein by reference.

FIELD OF THE INVENTION

The invention relates to a motion determination device, method and computer program for determining the motion of an object. The invention relates further to a magnetic resonance (MR) therapy system, method and computer program for treating the object based on the determined motion.

BACKGROUND OF THE INVENTION

The article "Ultrafast volumetric cine MRI (VC-MRI) for real-time 3D target localization in radiation therapy" by W. Harris et al., Proceedings of the International Society for Magnetic Resonance in Medicine, ISMRM, 24$^{th}$ Annual Meeting and Exhibition, Singapore, number 3210 (2016) discloses a deformation of a volumetric MR image based on a two-dimensional cine MR image, i.e. based on several MR images acquired at several acquisition times, and based on a patient Principle Component Analysis (PCA) based respiratory breathing model.

The article "Automatic Correction of Motion Artifacts in Magnetic Resonance Images Using an Entropy Focus Criterion" by D. Atkinson et al., IEEE Transactions of Medical Imaging, volume 16, pages 903 to 910 (1997) discloses an automatic correction of motion artifacts in MR images using an entropy focus criterion.

It is known from, for instance, the article "Hybrid two-dimensional navigator correction: a new technique to suppress respiratory-induced physiological noise in multi-shot echo-planar functional MRI" by R. L. Barry et al., Neuro-Image, volume 39, pages 1142-1150 (2008) that several MR images of a moving object can be generated for different times and that these MR images can be registered to each other for determining the motion of the object. This process of determining the motion of the object allows for a motion determination with a relatively low temporal resolution only.

SUMMARY OF THE INVENTION

It is therefore an object of the present invention to provide a motion determination device, method and computer program which allow for a determination of a motion of an object with an increased temporal resolution. It is a further object of the present invention to provide an MR therapy system, method and computer program for treating the object depending on the determined motion.

In a first aspect of the present invention a motion determination device for determining the motion of an object is presented, wherein the motion determination device comprises:

an MR information providing unit for providing an MR image of the object and for providing non-image MR data of the object, wherein the non-image MR data have been acquired at different acquisition times and are k-space data, a motion determination unit for determining a motion field, which describes the motion of the object, depending on the provided non-image MR data acquired at the different acquisition times and the provided MR image.

Since the motion determination unit just needs the provided MR image and the provided non-image MR data acquired at the different acquisition times and not several MR images for determining the motion field and hence the motion of the object, it is not required to, for instance, acquire a relatively large amount of k-space data at the different acquisition times, to reconstruct several MR images for the different acquisition times based on the acquired k-space data and to register the reconstructed several MR images for determining the motion. This allows for an increased temporal resolution of the determination of the motion of the object.

The object is preferentially a living being, i.e. a person or an animal, or a part of the living being such as an organ like the heart, the lung, the pancreas, the kidney, et cetera. The object can also be a technical object. The motion field is preferentially a three-dimensional motion field describing the motion in three spatial dimensions. However, the motion field can also be a two-dimensional motion field describing the motion in two spatial dimensions.

The motion determination unit is not adapted to use the non-image MR data for reconstructing several MR images for the different acquisition times and to then determine the motion field based on the reconstructed several MR images. The motion determination unit is adapted to directly use the non-image MR data, which are k-space data, for determining the motion field, i.e. without an intermediate reconstruction of MR images based on the non-image MR data. The motion of the object, which is determined by the motion determination unit, is therefore a motion of the object between the different acquisition times at which the non-image MR data have been acquired. The determined motion field can therefore describe the motion of the object over a time period spanning the different acquisition times at which the non-MR data being the k-space data have been acquired.

The MR information providing unit can be a storage in which the non-image MR data and the MR image are stored and from which the non-image MR data and the MR image can be retrieved for providing the same. The MR information providing unit can also be a receiving unit for receiving the non-image MR data and the MR image and to provide the received non-image MR data and the MR image. For instance, the MR information providing unit can be adapted to receive the non-image MR data from an MR data acquisition device and the MR image from an MR image generating unit being adapted to generate an MR image based on MR data acquired by the MR data acquisition device. The MR information providing unit can also be the MR data acquisition device with the MR image generating unit. The MR data acquired by the MR data acquisition device and used for reconstructing the MR image are preferentially k-space data. Also the non-image MR data are k-space data.

In an embodiment the motion determination device further comprises a dynamic MR image generating unit for generating a dynamic MR image of the object based on the provided MR image and the determined motion field. A dynamic MR image of the object can be regarded as a sequence of different static MR images for different times, wherein the sequence of static MR images shows the motion of the object during a time period covered by the different times. Thus, the dynamic MR image of the object, which is generated based on the provided MR image and the determined motion field, shows the motion of the object over a time period spanning the different acquisition times at which the non-image MR data being k-space data have been acquired. Since for generating a respective static MR image at a respective time it is not required to acquire, for instance, a relatively large amount of k-space data at the respective time which would generally be required for reconstructing a static MR image for the respective time, but it is just required to, for instance, acquire the relatively few non-image MR data at the respective time, a significant reduction of the time needed for acquiring the MR data needed for generating the dynamic MR image can be achieved, thereby allowing for an increased temporal resolution of the dynamic MR image.

The MR image provided by the MR information providing unit can be named "reference MR image". The reference MR image is preferentially a static MR image. The reference MR image can be reconstructed based on MR data which have been acquired at a certain acquisition time or at a certain motion phase while the object is moving or based on MR data which have been acquired while the object was not moving. Moreover, the MR information providing unit is preferentially configured to provide a steady-state MR image, i.e. a steady-state magnetization MR image, as the reference MR image and/or to provide steady-state non-image MR data, i.e. steady state magnetization non-image MR data, as the non-image MR data. Thus, the non-image MR data are preferentially k-space data which have been acquired during a readout interval during which the magnetization was in a steady-state condition. Moreover, the provided MR image has preferentially been reconstructed based on k-space data which have been acquired during a readout interval in which the magnetization was in a steady-state condition. Furthermore, preferentially both, i.e. a) the k-space data being the non-image MR data and b) the k-space data being used for reconstructing the provided MR image, are acquired during a same steady-state regime, that is, by using the same kind of sequence. If the provided reference MR image is a steady-state MR image and if the non-image MR data are steady-state non-image MR data, the determined motion is less influenced by dynamic magnetic processes. This can lead to an improved accuracy of the determined motion.

The MR information providing unit is configured to provide k-space data as the non-image MR data. Thus, the MR image providing unit is configured to provide different sets of k-space data as the non-image MR data, wherein the different sets of k-space data, i.e. the different k-space data sets, have been acquired at different acquisition times. The motion determination unit is configured to determine the motion field depending on the provided k-space data sets acquired at the different acquisition times and the provided MR image. In particular, the MR information providing unit is preferentially configured to provide k-space data which do not completely fill the k-space such that the provided k-space data are undersampled as compared to k-space data which have been used for generating the provided MR image. In particular, the spatial resolution of the provided MR image defines the resolution, i.e. the data points, of the k-space due to the Nyquist criterion. Thus, preferentially the spatial resolution of the provided MR image together with the Nyquist criterion defines the fully sampled k-space. The non-image MR data do not need to respect this sampling scheme, i.e. they do not need to be in accordance with the Nyquist criterion, and can be acquired in much sparser fashion. In an embodiment the MR information providing unit is configured to provide the k-space data, i.e. the non-image k-space data, such that they fill less than 5 percent of the k-space, i.e. less than 5 percent of the full space, further preferred less than 1 percent of the k-space, i.e. further preferred less than 1 percent of the full k-space. Thus, at each acquisition time respective k-space data can be acquired, which fill less than 5 percent, further preferred less than 1 percent, of the full k-space. In particular, the k-space is formed by data point positions at which data points, i.e. k-space data, can be acquired. The reference MR image, i.e. the provided MR image, is preferentially reconstructed based on k-space data for all data point positions, i.e. based on a completely filled k-space. The non-image k-space data, which fill less than 5 percent of the full k-space, preferentially correspond to less than 5 percent of all data point positions of the full k-space. In other words, the number of data point positions in the k-space, for which non-image k-space data are acquired at a certain acquisition time for determining the motion field, is preferentially less than 5 percent of the number of data point positions in the full k-space, for which k-space data are acquired, which are used for reconstructing the reference MR image. By using such few k-space data, the acquisition time can be further decreased. This can lead to a further increased temporal resolution of the determination of the movement of the object.

The k-space data being the non-image MR data are acquired with gradient fields and hence with spatial encoding. However, as explained above, these k-space data are preferentially undersampled, i.e. below the Nyquist rate, wherein this does not matter, because, as also explained above, these k-space data, i.e. the non-image MR data, are not used for reconstructing images which in turn are used for determining a motion field, but these k-space data are directly used for determining the motion field. Moreover, the provided MR image and the non-image MR data do not need to originate from a same acquisition. Thus, in an embodiment the provided MR image and the non-image MR data originate from different acquisitions, wherein also in this case preferentially both, i.e. a) the k-space data being the non-image MR data and b) the k-space data being used for reconstructing the provided MR image, are acquired during a same steady-state regime, that is, by using the same kind of sequence.

It is further preferred that the MR information providing unit is configured to provide the k-space data such that they form a spiral-like trajectory in the k-space. If the k-space data acquired at a respective time form a spiral-like trajectory, the motion can be determined with a further increased accuracy. However, the k-space data can also be provided such that they form a trajectory having another shape in the k-space.

In a preferred embodiment the motion determination device further comprises a) a motion model providing unit for providing a motion model which models the motion field, and b) a non-image MR data function providing unit for providing a non-image MR data function describing non-image MR data for different acquisition times depending on an MR image and depending on the provided motion model, wherein the motion determination unit is configured to determine the motion field by adapting the motion model such that the non-image MR data function yields the provided non-image MR data at the different acquisition times given the provided MR image. By using the motion model and the non-image MR data function and by determining the motion field and hence the motion by adapting the motion model such that the non-image MR data function yields the provided non-image MR data acquired at the different acquisition times given the provided MR image, the motion can be determined with a further increased accuracy and with relatively low computational efforts.

In a preferred embodiment the non-image MR data function providing unit is configured to provide the non-image MR data function in accordance with $$s^j(k) = \int_{R^3} q(r)\exp(-i2\pi k \cdot u^j(r))dr, \quad (1)$$

wherein $s^j$ denotes the non-image MR data for an acquisition time indicated by the index j, q(r) denotes MR image values of the provided reference MR image at different spatial positions r, k denotes the gradient trajectory in the k-space and $u^j(r)$ denotes the motion model defining a spatial position of a part of the object, which is indicated by the respective spatial position r, at the acquisition time indicated by the index j. The reference MR image q(r) can be defined in accordance with following equation:

$$q(r)=\rho(r)m(r), \quad (2)$$

wherein ρ(r) denotes the spin density of the object at the spatial position r and m(r) is a variable being indicative of the unit magnetization (i.e. with static MR equilibrium condition m=(0,0,1)) at the spatial position r.

The motion determination unit can be adapted to use exactly equation (1) or to use an approximation of this equation as the non-image MR data function. By using this specific non-image MR data function exactly or approximately the accuracy of determining the motion of the object can be further increased.

In an embodiment the motion model providing unit is configured to provide an affine motion model as the motion model. Moreover, in an embodiment the motion determination unit is configured to use a gradient-based minimization algorithm, especially a Newton-type minimization algorithm, for adapting the motion model such that the non-image MR data function yields the provided non-image MR data acquired at the different acquisition times given the provided MR image.

In a further aspect of the present invention an MR therapy system for treating an object being a living being or a part of a living being is presented, wherein the MR therapy system comprises:

a motion determination device for determining a motion of the object as defined in claim 1, a treating device for treating the object depending on the determined motion.

In an embodiment the treating device is configured to emit treating energy in the direction of the object under consideration of the determined motion. In particular, the treating device can comprise a linear particle accelerator (LINAC) for emitting the treating energy in the direction of the object. Since the motion can be determined with an increased temporal resolution and since the treating device treats the object depending on this determined motion, the treating device can more accurately react to the movements of the object, thereby leading to an improved quality of treating the object with reduced therapy side effects.

In another aspect of the present invention a motion determination method for determining the motion of an object is presented, wherein the motion determination method comprises:

providing an MR image of the object and providing non-image MR data of the object, wherein the non-image MR data have been acquired at different acquisition times and are k-space data, by an MR information providing unit, determining a motion field, which describes the motion of the object, depending on the provided non-image MR data for the different times and depending on the provided MR image by a motion determination unit.

In an aspect of the present invention an MR therapy method for treating an object being a living being or a part of a living being is presented, wherein the MR therapy method comprises:

determining a motion of the object as defined in claim 11, treating the object depending on the determined motion by using a treating device.

In a further aspect of the present invention a computer program for controlling a motion determination device as defined in claim 1 is presented, wherein the computer program comprises program code means for causing the motion determination device to carry out the motion determination method as defined in claim 11, when the computer program is run on a controller controlling the motion determination device.

In another aspect of the present invention a computer program for controlling an MR therapy system as defined in claim 9 is presented, wherein the computer program comprises program code means for causing the MR therapy system to carry out the MR therapy method as defined in claim 12, when the computer program is run on a controller controlling the MR therapy system.

It shall be understood that the motion determination device of claim 1, the MR therapy system of claim 9, the motion determination method of claim 11, the MR therapy method of claim 12, the computer program for controlling a motion determination device of claim 13 and the computer program for controlling an MR therapy system of claim 14 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
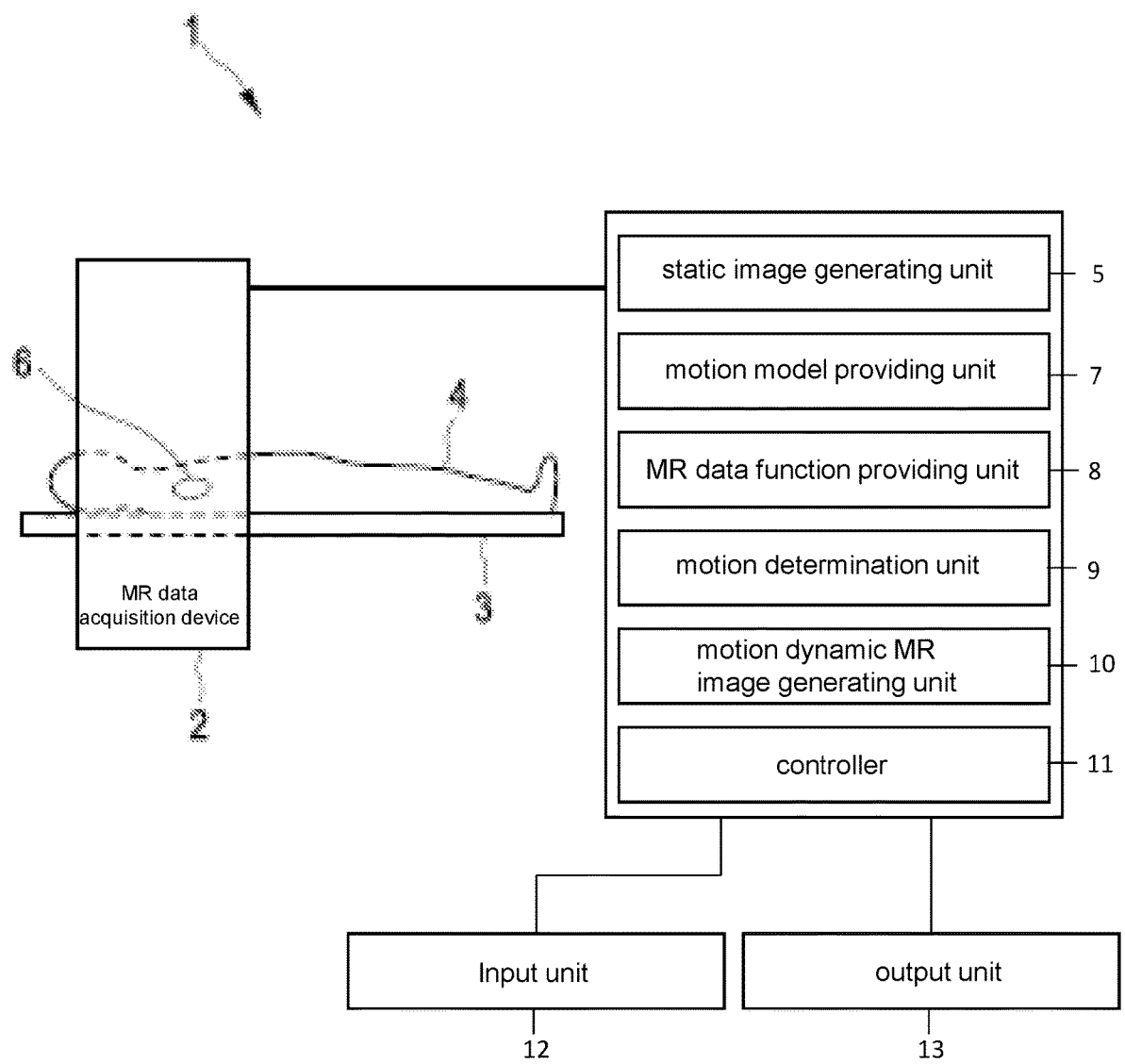
FIG. 1 shows schematically and exemplarily an embodiment of a motion determination device for determining the motion of an object.

FIG. 1 shows schematically and exemplarily an embodiment of a motion determination device for determining the motion of an object. In this embodiment the motion determination device 1 is an MR imaging system. The MR imaging system 1 comprises an MR data acquisition device 2 for acquiring MR data being k-space data of a heart 6 of a person 4 lying on a support means 3 like a patient table. In particular, the MR data acquisition device 2 is adapted to acquire k-space data being sufficient for reconstructing a three-dimensional static steady-state MR image of the heart 6. This reconstruction is carried out by a static image generating unit 5 of the MR imaging system 1. For reconstructing the static steady-state MR image, which can also be regarded as being a reference MR image, the k-space is preferentially completely filled with k-space data, wherein these k-space data are then preferentially used by the static image generating unit 5 for generating the reference image.

The MR data acquisition device 2 is further adapted to acquire k-space data at different acquisition times, wherein these k-space data are not used by the static image generating unit 5 for generating a respective static MR image for the respective acquisition time. In fact, these k-space data acquired at different acquisition times are provided to a motion determination unit 9 together with the static reference MR image generated by the static image generating unit 5 for allowing the motion determination unit 9 to determine a motion field, which describes the motion of the heart 6, depending on the k-space data acquired at the different times and the static reference MR image. Also the k-space data acquired at the different times are preferentially steady-state data.

Steady-state magnetization preferentially refers to a magnetization state being repeatedly acquired after each repetition of a radiofrequency excitation. This state is thus the same for each repetition. Steady-state k-space data are preferentially data acquired during a read-out interval when the magnetization is in the steady state. A steady-state MR image is preferentially an image formed from steady-state k-space data.

The k-space data, which are not used for generating the static reference MR image, i.e. the non-image MR data which are acquired at the different acquisition times, do not completely fill the k-space. Preferentially at the respective acquisition time the k-space data fill less than 5 percent of the k-space. In particular, the k-space is formed by data point positions at which data points, i.e. k-space data, can be acquired. The static reference MR image is preferentially reconstructed based on k-space data for all data point positions, i.e. based on a completely filled k-space. The k-space data, which fill less than 5 percent of the k-space, preferentially correspond to less than 5 percent of all data point positions of the k-space. In other words, the number of data point positions in the k-space, for which k-space data are acquired at a certain acquisition time, is preferentially less than 5 percent of the number of data point positions in the k-space, for which k-space data are acquired, which are used for reconstructing the static reference MR image. In an embodiment the k-space data form a trajectory within the k-space at the respective acquisition time having a spiral-like shape.

The MR imaging system 1 further comprises a motion model providing unit 7 for providing a motion model which models the motion field and a non-image MR data function providing unit 8 for providing a non-image MR data function describing non-image MR data, i.e. k-space data, for different acquisition times depending on an MR image like a static reference MR image and depending on the provided motion model. The motion determination unit 9 is preferentially configured to determine the motion field and hence the motion of the heart 6 by adapting the provided motion model such that the non-image MR data function yields the provided k-space data for the different acquisition times given the static MR reference image generated by the static image generating unit 5. In particular, the non-image MR data function providing unit 8 is adapted to provide the non-image MR data function in accordance with above mentioned equation (1).

Thus, the motion determination unit 9 can be configured to adapt the motion model $u^j(r)$, which could also be regarded as being a transformation function, such that under consideration of the static reference MR image, which has been reconstructed by the static image generating unit 5, the non-image MR data function defined by equation (1) yields the k-space data acquired at the several acquisition times by the MR data acquisition device 2. During this adaptation process equation (1) is preferentially approximated, wherein the motion model can be an affine motion model or another motion model. For the adaptation a gradient-based minimization algorithm, especially a Newton-type minimization algorithm, or another algorithm might be used.

The MR imaging system 1 further comprises a dynamic MR image generating unit 10 for generating a dynamic MR image of the heart 6 based on the static MR image generated by the static image generating unit 5 and based on the determined motion field, i.e. based on the adapted motion model $u^j(r)$. The generated dynamic MR image of the heart may be used for showing the dynamic behavior of the heart wall, thereby revealing insights about stress and strain.

The MR imaging system 1 also comprises an input unit 12 like a keyboard, a computer mouse, a touchpad et cetera and an output unit 13 like a display. Moreover, the imaging system 1 comprises a controller 11 for controlling the different components of the MR imaging system 1.

Figure 2:
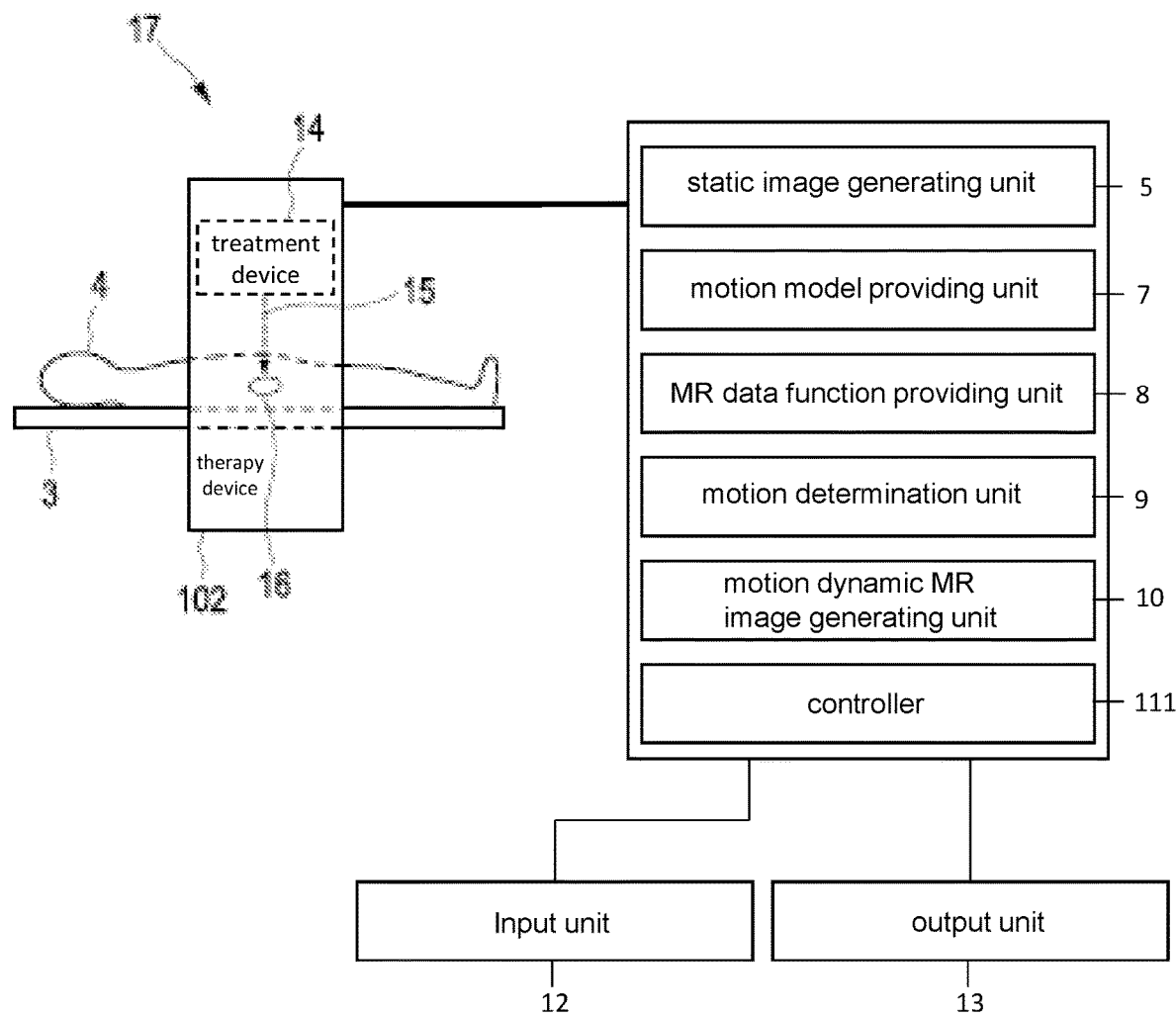
FIG. 2 shows schematically and exemplarily an embodiment of an MR therapy system for treating an object.

FIG. 2 shows schematically and exemplarily an embodiment of an MR therapy system for treating an object. In this embodiment the object 16 is a kidney of a person 4 lying on a support means 3. The MR therapy system 17 comprises an MR data acquisition and therapy device 102 being a combination of an MR data acquisition device 2 for acquiring MR data like k-space data and of a treating device 14 for treating the kidney 16 by treating energy 15 emitted by the treating device 14. Similar to the MR imaging system 1 described above with reference to FIG. 1, the MR therapy system 17 comprises a static image generating unit 5, a motion model providing unit 7, a non-image MR data function providing unit 8, a motion determination unit 9 and a dynamic MR image generating unit 10. The MR therapy system 17 also comprises a controller 111 for controlling the different components of the MR therapy system 17, particularly the MR data acquisition and the treating device 14 for treating the kidney 16 depending on the determined motion of the kidney 16. In particular, the treating device 14 is controlled such that the treating energy 15 is always directed to the kidney 16, even if the kidney 16 moves. Thus, the determined motion, particularly three-dimensional motion fields of organs and tumors, can be used to steer a treating irradiation. In this embodiment the treating device 14 is a LINAC generating x-rays or high energy electrons for treating the kidney depending on the determined motion of the kidney. Also the MR therapy system 17 comprises an input unit 12 like a keyboard, a mouse, a touchpad, et cetera and an output unit 13 like a display.

Figure 3:
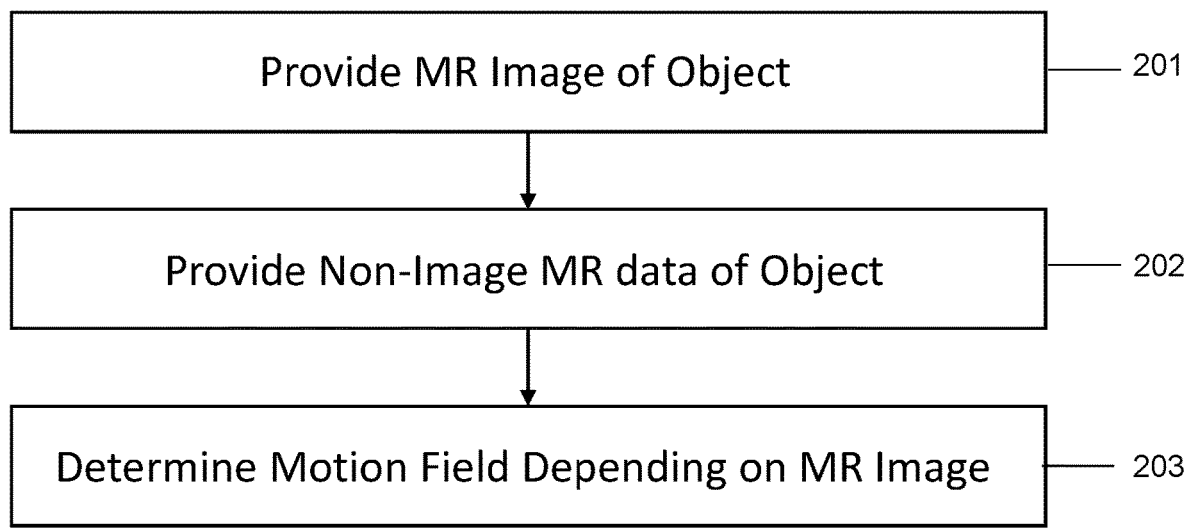
FIG. 3 shows a flowchart exemplarily illustrating an embodiment of a motion determination method for determining the motion of an object.

In the following an embodiment of a motion determination method for determining the motion of an object will exemplarily be described with reference to a flowchart shown in FIG. 3.

In step 201 an MR image of the object is provided. Thus, for instance, the MR data acquisition device 2 or the MR data acquisition and therapy device 102 acquire k-space data of the object at a certain time, wherein these k-space data are used for generating a static image of the object. The provided MR image can also be a static MR image showing the object in a certain motion phase, wherein for generating this static MR image k-space data might be used which have been acquired at different acquisition times, but in the same certain motion phase. For this purpose, known gating techniques can be used. The provided MR image can be regarded as being a reference MR image.

In step 202 the non-image MR data of the object are provided, which have been acquired at different acquisition times. In particular, the MR data acquisition device 2 or the MR data acquisition and therapy device 102 acquire k-space data at the different acquisition times. The k-space data acquired at the different acquisition times are preferentially not sufficient for reconstructing an MR image for the respective acquisition time, i.e. at the respective acquisition time only a few k-space data are preferentially acquired which form a trajectory within the k-space, which might be spiral-like or which might have another shape.

In step 203 a motion field, which describes the motion of the object, is determined depending on the MR image provided in step 201 and depending on the non-image MR data provided in step 202. In particular, a motion model, which models the motion field of the object, and a non-image MR data function describing non-image MR data for different acquisition times depending on an MR image and depending on the motion model can be provided, wherein the motion field and hence the motion of the object can be determined by adapting the motion model such that the provided non-image MR data function yields the non-image MR data provided in step 202 for the different acquisition times given the MR image provided in step 201.

Figure 4:
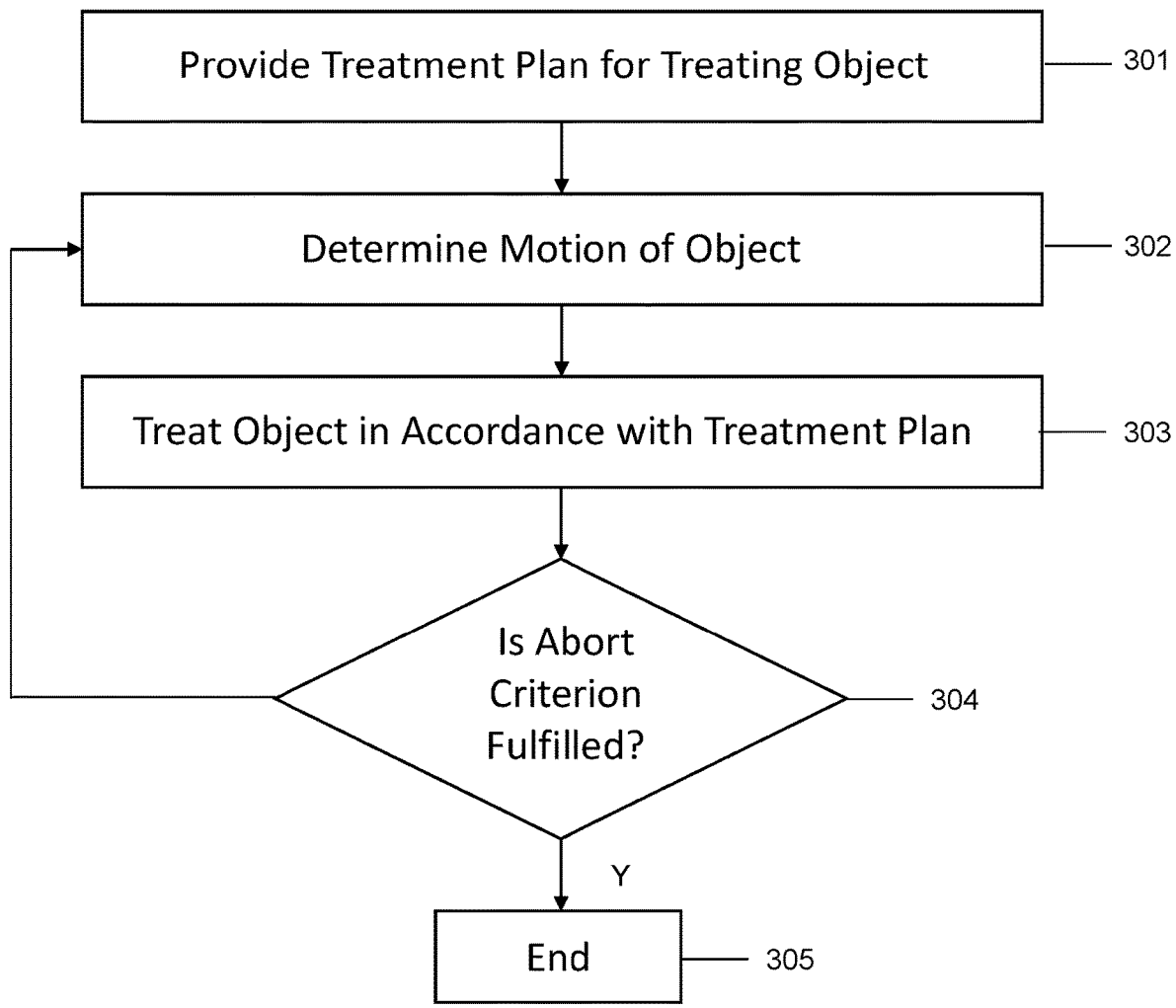
FIG. 4 shows a flowchart exemplarily illustrating an embodiment of an MR therapy method for treating an object, FIG. 5 schematically and exemplarily illustrates organ deformation modeled as a change of variables transformation, FIG. 6 schematically and exemplarily illustrates the direct use of k-space data for the motion determination, FIG. 7 schematically and exemplarily illustrates a prior art motion determination procedure being based on image registration, FIG. 8 schematically and exemplarily illustrates a three-dimensional spiral k-space trajectory, and FIG. 9 schematically and exemplarily illustrates a steady-state MR sequence usable for acquiring k-space data.

In the following an embodiment of an MR therapy method for treating an object will exemplarily be described with reference to a flowchart shown in FIG. 4.

In step 301 a treatment plan is provided defining a treatment of the object by using treating energy. For instance, the treatment plan can define which part of the object should be irradiated with which intensity of a treating radiation emitted by the treating device 14 of the MR data acquisition and therapy device 102. In step 302 the motion of the object is determined in accordance with, for instance, the motion determination method described above with reference to FIG. 3. In step 303 the object is treated in accordance with the treatment plan provided in step 301 under consideration of the motion determined in step 302. In particular, radiation or particles emitted by the treating device 14 of the MR data acquisition and therapy device 102 is directed to the moving object in accordance with the treatment plan provided in step 301. In step 304 it is determined whether an abort criterion is fulfilled, wherein, if this is the case, the MR therapy method ends in step 305. Otherwise, the MR therapy method continues with step 302. Thus, in a loop the motion of the object is determined and the object is treated under consideration of the determined motion until the abort criterion is fulfilled. The abort criterion is, for instance, whether it has been indicated by a user like a physician that the MR therapy method should stop via the input unit 12, whether the treatment defined in the treatment plan has been carried out completely, et cetera.

In the following the motion model $u^j$, which may also be regarded as being a transformation function, will be illustrated with reference to FIG. 5.

Figure 5:
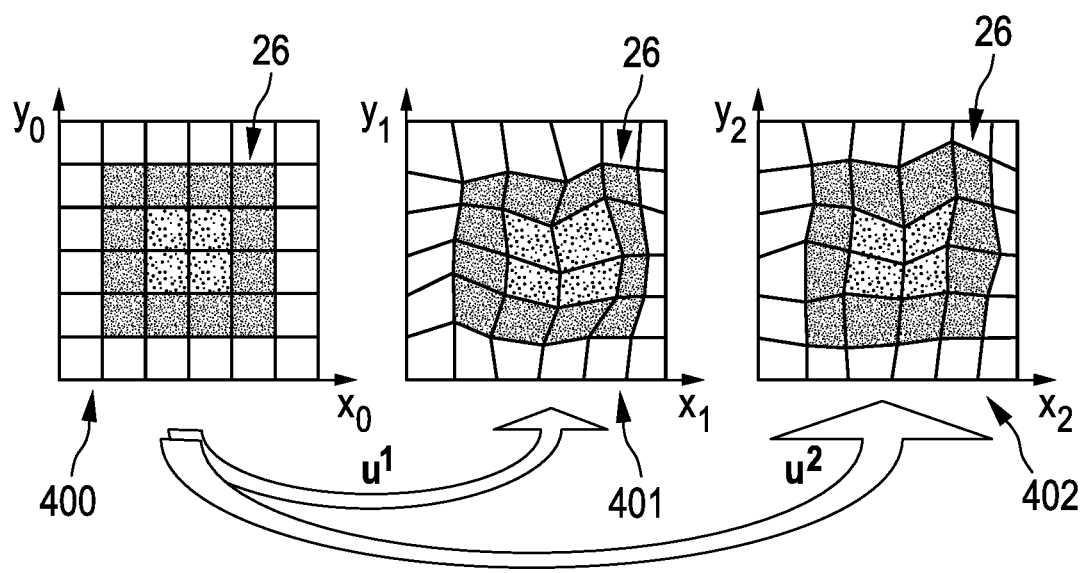

In FIG. 5 an object 26 like an organ is defined on a respective coordinate system 400, 401, 402 at three different times. As can be seen in FIG. 5, at a time $t_1$ (corresponds to coordinate system 401) the object 26 has been moved, i.e. in this example has been deformed, and at a time $t_2$ (corresponds to coordinate system 402) the object 26 has been further moved, i.e. has been further deformed. The deformations of the object 26 and hence of the respective coordinate grid are described by respective transformations $u^1$, $u^2$, wherein these transformations form a time-depended transformation function or adapted motion model which is generally denoted $u^j$ as explained above with reference to, for instance, equation (1). Since the motion model $u^j$ has a low-dimensional information content, minimal data are sufficient for its reconstruction. The acquisition time period for acquiring MR data, i.e. k-space data, at a certain acquisition time can therefore be ultra-short. Once the motion model $u^j$ has been adapted, i.e. once the adapted motion model and hence the motion field are known, dynamic three-dimensional images immediately follow.

The motion model is preferentially a low dimensional model of the motion field and hence of the motion of the object, wherein preferentially motion also includes deformation of the object. The expression "low dimensional" refers to the number of parameters of the motion model, which are adapted for adapting the motion model such that the non-image MR data function yields the provided non-image MR data at the different acquisition times given the provided MR image, i.e. given the provided static reference MR image. The number of parameters of the motion model is much smaller than the number of image elements, which are preferentially voxels, in the reference MR image. In a preferred embodiment the number of parameters of the model is less than 5 percent of the number of image elements of the reference image.

The term "static" means that the MR image does not show the movement of the object. This might be because, for instance, the object really does not move while acquiring the MR data used for reconstructing the reference MR image, or because it shows the object in a single motion phase, if the motion is periodic, or because MR data are used for the reconstruction of the reference MR image, which have been acquired at a single time point.

The MR imaging system and the MR therapy system described above with reference to FIGS. 1 and 2 reconstruct the motion model, which might also be regarded as being a transform function, by directly fitting the motion model to the non-image MR data which are preferentially time-domain data. This will in the following be further illustrated with reference to FIG. 6.

Figure 6:
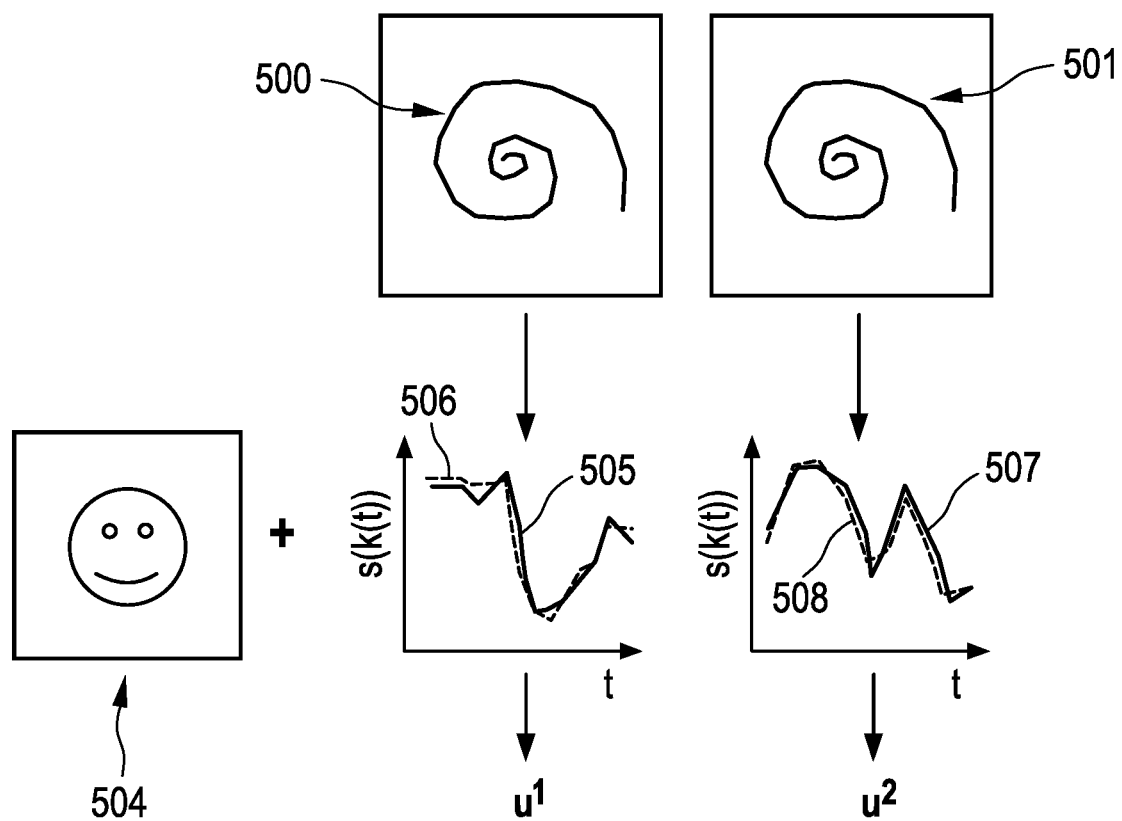

K-space data 505 are acquired along a spiral-type trajectory 500 for an ultra-short acquisition time. It should be noted that s(k(t)) shown in FIG. 6 and $s^j(k)$ mentioned in equation (1) denote the same parameter, i.e. the k-space data at the respective acquisition time indicated by j. Since the acquisition along the k-space directory 500 is ultra-short, the respective acquisition time, at which the ultra-short k-space acquisition is carried out, can be regarded as being a time point. Alternatively, a certain time point within the ultra-short time period needed for acquiring the k-space data along the trajectory 500 can be regarded as being the respective acquisition time. For instance, the center of this ultra-short time period could be regarded as being the respective acquisition time indicated by the index j. At a further acquisition time further k-space data 507 are acquired along the k-space trajectory 501, wherein the k-space trajectories used at different acquisition times are preferentially the same. After the motion determination unit has determined the motion field and hence the motion of the object by adapting the motion model $u^j$ given the reference MR image 504, the non-image MR data function, which is shown in FIG. 6 by the curves 506, 508, yields the measured k-space data indicated in FIG. 6 by the curves 505, 507.

Figure 7:
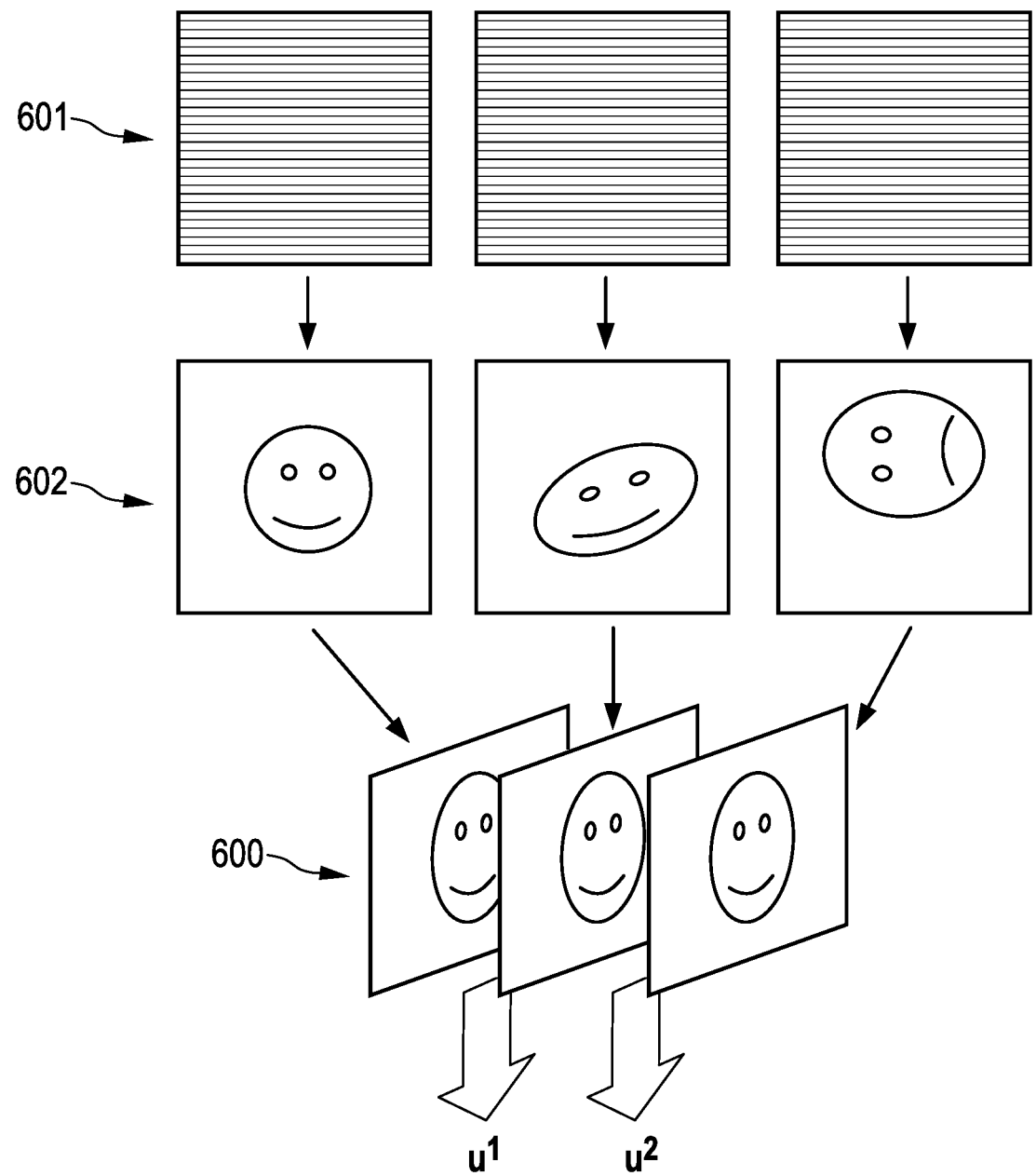

This is in contrast to the prior art illustrated in FIG. 7. In the prior art at different acquisition times several corresponding sets of k-space data 601 are acquired. At the respective acquisition time the k-space needs to be filled completely or almost completely as indicated by the several lines within the rectangles 601, in order to allow for a reconstruction of static MR images 602. These static MR images are then registered as indicated by reference sign 600 wherein this registration yields the motion model $u^j$. Thus, at each acquisition time many k-space data 601 need to be acquired, thereby leading to a relatively low temporal resolution. Moreover, the generated static MR images need to be registered for determining the motion model, wherein the registration can be time consuming and can introduce errors in the finally determined motion model. In contrast to this, the motion determination procedure described above with reference to FIGS. 1 to 5 does not need an acquisition of many k-space data for generating a respective static MR image at each acquisition time. Only a single static reference image, which may correspond to a certain motion phase of the object, is needed. The resulting very high temporal resolution of the motion determination allows, for instance, monitoring cardiac contraction dynamics or tracking kidneys and/or pancreas during an MR-LINAC radiotherapy session. The motion determination procedure described above with reference to FIGS. 1 to 5 also allows for a determination of the motion with a high clinical quality spatial resolution.

In the following equation (1) will be explained in more detail. The MR phenomenon can be described by the Bloch equation:

$$\frac{d}{dt}M = \begin{pmatrix} -\frac{1}{T_2} & \gamma(G\cdot r + \Delta B_0) & -\gamma B_{1,y} \\ -\gamma(G\cdot r + \Delta B_0) & -\frac{1}{T_2} & \gamma B_{1,x} \\ \gamma B_{1,y} & -\gamma B_{1,x} & -\frac{1}{T_1} \end{pmatrix} M + \begin{pmatrix} 0 \\ 0 \\ \frac{M_0}{T_1} \end{pmatrix}, \quad (3)$$

$$M(0) = \begin{pmatrix} 0 \\ 0 \\ M_0 \end{pmatrix},$$

wherein $M(t,r) \equiv (M_x(t,r), M_y(t,r), M_z(t,r))^T$ is the spin magnetization, $M_0(r)$ is the equilibrium value, directly proportional to the proton spin density, $\rho$, $T_1(r)$ and $T_2(r)$ are tissue relaxation parameters, $\Delta B_0(r)$ is the off-resonance, $G(t) \equiv (G_x(t), G_y(t), G_z(t))^T$ is the applied gradient field, $\gamma$ is the gyromagnetic constant, $B_{1,x}(t,r) \equiv \Re\{B_1^+(r)RF(t)\}$ and $B_{1,y}(t,r) \equiv \Im\{B_1^+(r)RF(t)\}$, wherein $RF(t) \in \mathbb{C}$ is the excitation radio frequency waveform and $B_1^+$ is the spatially varying transmit magnetic field. For simplicity of exposition, it is considered $B_1^+ \in \mathbb{R}$, however, in practice $B_1^+ \in \mathbb{C}$. The equations can be easily extended to this case.

It is useful to scale the magnetization in equation (3) in the following way. Set $$m \equiv \frac{M}{M_0},$$

then it can be easily shown that equation (3) can be written as:

$$\frac{d}{dt}m = \qquad (4)$$

$$\begin{pmatrix} -\frac{1}{T_2} & \gamma(G\cdot r + \Delta B_0) & -\gamma B_{1,y} \\ -\gamma(G\cdot r + \Delta B_0) & -\frac{1}{T_2} & \gamma B_{1,x} \\ \gamma B_{1,y} & -\gamma B_{1,x} & -\frac{1}{T_1} \end{pmatrix} m + \begin{pmatrix} 0 \\ 0 \\ \frac{1}{T_1} \end{pmatrix} \text{ with } m(0) = \begin{pmatrix} 0 \\ 0 \\ 1 \end{pmatrix}.$$

It can thus be seen that $M_0$ is eliminated from the Bloch equation for the scaled vector m. For ease of notation, it is made use of the compact form for equation (4):

$$\frac{d}{dt}m = \prod m + c, \qquad (5)$$

with $m(0) = (0, 0, 1)$ and $m \equiv \frac{M}{M_0}$.

Preferentially, a steady-state MR sequence is applied to the object for acquiring the MR data used for detecting the motion. The steady-state MR sequence employs preferentially short, single-shot spiral read-out gradients which are fully balanced. The repetition time is given by $T_R$ and the time of acquiring spiral k-space data at a respective acquisition time is $T_A$ where $T_A \ll T_R$. It can also be assumed that $T_A \ll T_1$ and $T_A \ll T_2$ thus the transverse and longitudinal decay effects are negligible during readout. The signal at the j-th acquisition time is given by:

$$s^j(k) = \int_{R^3} \rho^j(r_1) m^j(r_1) e^{-i2\pi k \cdot r_1} dr_1, \qquad (6)$$

wherein $k \equiv (k_x, k_y, k_z)$ denotes the gradient trajectory, i.e. the k-space trajectory, $\rho^j$ is the spin density and $m^j$ is the scaled transverse magnetization (see equation (5)) at the beginning of the acquisition. For ease of notation, the global constant of proportionality between $s^j(k)$ and the integral on the right hand side is neglected.

It is preferentially supposed that the object is deformed in the time occurring between two steady state acquisitions, that is, there is a (nonlinear) transformation u defined by $r_2 = u(r_1)$ with $r_1 = (x_1, y_1, z_1)$ and $$r_2 = (x_2, y_2, z_2) = (u_x(x_1, y_1, z_1), u_y(x_1, y_1, z_1), u_z(x_1, y_1, z_1))$$

denoting the geometry before and after the deformation, respectively, wherein u is the motion model which models a motion field and hence the motion being a deformation in this example. The motion model can also be regarded as being a deformation function in this example. The time period $T_A$ is in the order of few milliseconds such that it is preferentially assumed that there is no displacement during the acquisition and that the displacement has a noticeable effect only over the $T_R$ interval. The signal from the deformed object in the new acquisition will therefore be:

$$s^{j+1}(k) = \int_{R^3} \rho^{j+1}(r_2) m^{j+1}(r_2) e^{-i2\pi k \cdot r_2} dr_2 \qquad (7)$$
$$= \int_{R^3} \rho^{j+1}(u(r_1)) m^{j+1}(u(r_1)) e^{-i2\pi k \cdot u(r_1)} |J(u)| dr_1$$

wherein the change of variable formula for a multi-dimensional integral has been used and $J(u)$ is the Jacobian matrix of u with respect to $x_1$, $z_1$ and $y_1$:

$$J(u) = \begin{pmatrix} \frac{\partial u_x}{\partial x_1} & \frac{\partial u_x}{\partial y_1} & \frac{\partial u_x}{\partial z_1} \\ \frac{\partial u_y}{\partial x_1} & \frac{\partial u_y}{\partial y_1} & \frac{\partial u_y}{\partial z_1} \\ \frac{\partial u_z}{\partial x_1} & \frac{\partial u_z}{\partial y_1} & \frac{\partial u_z}{\partial z_1} \end{pmatrix}. \qquad (8)$$

The second form of Equation (7) reveals important insights in the signal evolution due to motion. First of all, the displacement is negligible over the $T_A$ interval. Furthermore, the spins represented by the magnetization component $m^{j+1}$ are subject to the same $T_1$, $T_2$, and off-resonance ($\Delta B_0$) effects of $m^j(r_1)$. Since in this example a steady-states condition is present, the equilibrium for the spins at $r_1$ is the same as the one for the spins which have now moved to $r_2$ (after all, they are the same spins), thus it can be set $m^{j+1}(u(r_1)) = m^j(r_1)$ and filling it into equation (7) yields:

$$s^{j+1}(k) = \int_{R^3} \rho^{j+1}(u(r_1)) m^j(r_1) e^{-i2\pi k \cdot u(r_1)} |J(u)| dr_1. \qquad (9)$$

The transmit and receive radiofrequency (RF) fields might be spatially varying, as it is the case in reality. If the RF fields vary between locations, the dynamics of the corresponding spins will be different. Nonetheless, it is preferentially assumed that the spatial variation of these fields between the neighboring locations $r_1$ and $r_2$ is negligible and thus the corresponding spin dynamics are approximately equal. In reality, at common MR imaging field strengths, which might be 3 Tesla, 1.5 Tesla or smaller, this is a reasonable assumption.

As a next step, it is preferentially assumed that the total number of spins for an infinitesimal volume element $dr_1$ which is deformed into $du(r_1) = |J(u)| dr_1$ does not change.

In other words, it is preferentially assumed that conservation of magnetization holds. This leads to following equality:

$$\rho^j(r_1) dr_1 = \rho^{j+1}(u(r_1)) |J(u)| dr_1 \qquad (10)$$

and it is thus obtained:

$$s^{j+1}(k) = \int_{R^3} \rho^j(r_1) m^j(r_1) e^{-i2\pi k \cdot u(r_1)} dr_1. \qquad (11)$$

In more general, it can be written:

$$s^j(k) = \int_{R^3} \rho(r) m(r) e^{-i2\pi k \cdot u^j(r)} dr \qquad (12)$$

where m without superscript indicates the steady-state if there were no motion (reference image) and $u^j$ is the deformation at the j-th acquisition. Equation (12) corresponds to equation (1).

Equations (1) and (12) relate the signal $s^j(k)$ of the j-th acquisition to the displacement function $u^j(r)$, i.e. the motion model, through the preferred steady-state reference MR image in the static (no-motion) case. The deformed image at the given acquisition is not needed to reconstruct the displacement, which is what one is really interested to during cine-MRI or other many applications. This approach has the advantage to directly target the quantity of interest, without need for a full image acquisition step. Since u has a relatively compact spatial and temporal frequency content, the reconstruction can effectively be carried out in the Fourier domain of u or in another low-dimensional representation space.

If in an embodiment only a rigid translation is assumed as the motion, this rigid translation can be described by a vector $p^j$, yielding $u^j(r) = r + p^j$, such that equation (12) reduces to, through the Fourier Transform shift theorem:

$$s^j(k) = \int_{R^3} \rho(r) m(r) e^{-i2\pi k \cdot (r + p^j)} dr = e^{-i2\pi k \cdot p^j} \int_{R^3} \rho(r) m(r) e^{-i2\pi k \cdot r} dr = e^{-i2\pi k \cdot p^j} s(k) \qquad (13)$$

which is the linear phase accrual of the initial k-space data, s(k).

In the following an exemplary embodiment of reconstructing the transformation u, i.e. of determining the motion model and hence the motion, in accordance with equation (12) will be described.

The static MR image, which in this embodiment could also be named reference MR image, can be denoted as $q(r) \equiv \rho(r) m(r)$, has been provided by the MR information providing unit and hence is known. At a certain point in time, i.e. at a respective acquisition time, a very short 3D spiral-out k-space trajectory acquisition is carried out. However, also a non-spiral trajectory can be used. In this embodiment the collected data is denoted by d. The transformation u can be reconstructed by discretizing and inverting equation (12), that is, by solving the nonlinear least squares problem:

$$u^* = \operatorname{argmin} \sum_{h=1}^{H} \left| \sum_{n=1}^{N} q_n e^{-i2\pi k_h \cdot u(r_n)} - d_h \right|^2. \qquad (14)$$

In the above equation n is the spatial discretization index referred to the grid point location and h is the k-space data point index. H and N denote, respectively, the total number of data and grid points. In general, N is of order ($10^5$) and H<<N and thus the problem is ill-posed since there are (much) fewer equations than unknowns.

In an embodiment it is tried to reduce the number of unknowns to be smaller than H. Model reduction techniques can be applied to find a low dimensional representation of u. One way to do this is, for instance, to represent u(r) as a spatial basis function expansion, denoted by ũ:

$$u(r) \approx \tilde{u}(a) \equiv \sum_{\lambda=1}^{L} a_\lambda u_\lambda(r), \qquad (15)$$

wherein $u_\lambda$ denotes the λ-th order spatial basis function and L is the dimension of reduced representation. $a \equiv (a_1, K, a_L)$ is the vector of expansion coefficients. The reconstruction problem becomes then:

$$a^* = \operatorname{argmin} \sum_{h=1}^{H} \left| \sum_{n=1}^{N} q_n e^{-i2\pi k_h \cdot \sum_{\lambda=1}^{L} a_\lambda u_\lambda(r_n)} - d_h \right|^2. \quad (16)$$

The problem defined by equation (16) can be solved by standard minimization algorithms for nonlinear least squares. To efficiently apply derivative-based methods (Newton-type), the partial derivatives of the H components with respect to the L parameters can be used. They can easily be computed:

$$\frac{\partial}{\partial a_i} \left\{ \sum_{n=1}^{N} q_n e^{-i2\pi k_h \cdot \sum_{\lambda=1}^{L} a_\lambda u_\lambda(r_n)} - d_h \right\} = \quad (17)$$

$$\sum_{n=1}^{N} (-i2\pi k_h \cdot u_i(r_n)) q_n e^{-i2\pi k_h \cdot \sum_{\lambda=1}^{L} a_\lambda u_\lambda(r_n)}$$

for i=1, K, L and h=1, K, H. The problem defined by equation (16) can be solved by using, for instance, the Matlab built-in trust-region-reflective algorithm.

In an embodiment the transform, i.e. the motion model, u is modelled as an affine transformation $r^+ \equiv u(r) = Ar + b$, wherein the matrix A can represent rotation and stretching/compression, particularly anisotropic stretching/compression, while the vector $b \in \mathbb{R}^3$ represents the spatial shift with respect to the original position.

In another embodiment equation (6) may be solved by using a non-parametric model, thus without having to express u(r) explicitly as a sum of basis functions as shown in equation (15). Starting from equation (14) a regularization can be used, in order to obtain a good solution. This allows to obtain a good solution, although the problem, which needs to be solved here, is typically underdetermined, i.e. there are more unknowns than data points, wherein in, for instance, a three-dimensional setting the number of unknowns is equal to three times the number of voxels, because the problem must be solved for three motion field components, i.e., in this example for $u_x u_y$ and $u_z$. The addition of the penalty term can be described by following equation, wherein u is the unknown:

$$u^* = \operatorname{argmin} \sum_{h=1}^{H} \left| \sum_{n=1}^{N} q_n e^{-i2\pi k_h \cdot u_n} - d_h \right|^2 + \lambda R(u) \quad (18)$$

In equation (18) R is the regularization function and λ is a real parameter which weights the regularizer, i.e. the penalty term, versus the objective. The real parameter is problem dependent and can be determined in different ways. For instance, by calibration or by solving the present problem for a set of different lambda values, i.e. for a set of different parameters λ, and by determining the right one as a trade-off between data discrepancy and norm of the solution. The latter approach is also called L-curve approach. The regularization function can be, for instance, a Tichonov regularization with first order spatial derivatives:

$$R(u) = \sum_{n=1}^{N} \|\nabla u_n\|_2^2, \quad (19)$$

a Tichonov regularization with second order spatial derivatives:

$$R(u) = \sum_{n=1}^{N} \|\nabla^2 u_n\|_2^2, \quad (20)$$

a Total Variation:

$$R(u) = \sum_{n=1}^{N} \|\nabla u_n\|_2, \text{ or} \quad (21)$$

an L1 regularization with compressed sensing:

$$R(u) = \|\Psi u\|_1, \quad (22)$$

where ψ is a sparsity transformation like a wavelets transform.

Figure 8:
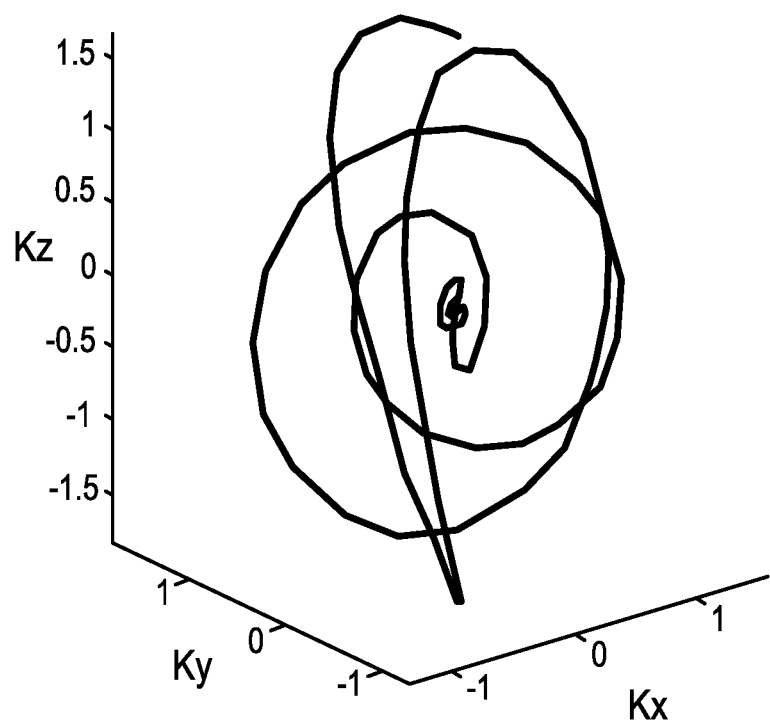

An exemplary k-space trajectory, along which the k-space data are acquired at a respective acquisition time, is shown in FIG. 8. The k-space data are collected at the respective acquisition time for a very short time being preferentially smaller than one millisecond.

Figure 9:
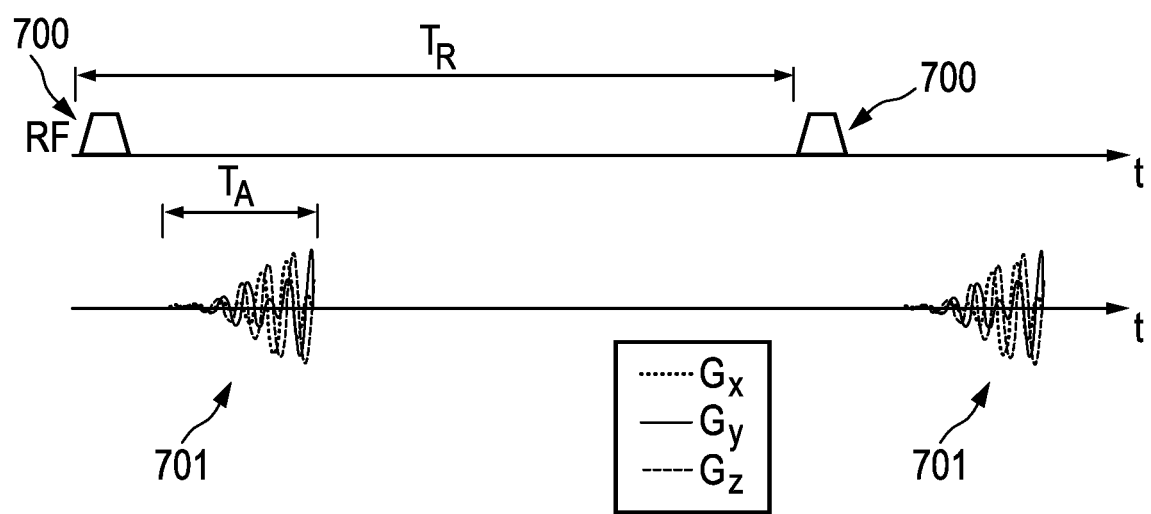

FIG. 9 schematically and exemplarily illustrates a steady-state MR sequence which might be used for acquiring the k-space data, i.e. the non-image MR data, at the different acquisition times. After each RF excitation 700 gradients 701 ($G_x$, $G_y$, and $G_z$), which might be spiral gradients, are applied for the signal acquisition during the time interval $T_A$. This procedure is repeated after the time period $T_R$, wherein $T_A \ll T_R$. For instance $T_A$ is five times smaller than $T_R$. In an exemplary embodiment $T_R$ might be about 20 ms and $T_A$ might be about 4 ms. Since the temporal distance between the different acquisition times is defined by $T_g$ and since $T_A \ll T_R$, the generation of the k-space data at a respective acquisition time can be regarded as being an acquisition at a single acquisition time point.

Although in above described embodiments the steady-state sequences are balanced, the steady-state sequences can also be non-balanced. For instance, the steady-state sequences can be spoiled ones. The steady-state sequence used for acquiring the k-space data at the several acquisition times can be, for instance, a spoiled gradient echo (GRE), a spin echo or an SSFP, particularly a bSSFP, sequence. In an embodiment gradient-echo steady-state sequences are used as disclosed, for instance, in chapter 14 of the "Handbook of MRI Pulse Sequences, 1st Edition" by Matt Bernstein, Kevin King, Xiaohong Zhou, Academic Press (2004) which is herewith incorporated by reference.

The k-space trajectories used at a respective acquisition time, which could also be named read-out trajectories, are preferentially ultra-short, wherein this means that the k-space data at a respective acquisition time are collected in a collection time being preferentially smaller than 10 ms, further preferred smaller than 4 ms and even further preferred smaller than 1 ms. During this very small collection time relaxation effects and organ motion can be neglected, i.e. the respective acquisition time, at which the k-space data are collected, can be regarded as being a single respective time point. As explained above, the motion of an object, which preferentially also includes a deformation of the object, can be indicated by the motion model or transform function u which modifies the object by changing the grid points to new coordinates given by $r_2 = u(r_1)$. The motion model or transform function u can be determined as described above by using, for instance, equation (1) or a corresponding discretized equation. Since it is not necessary to reconstruct, for instance, a deformed MR image at each acquisition time, the determination of the motion by determining the motion model or transform function u requires less MR data. For instance, the motion determination method described above with reference to FIGS. 1 to 5 can lead to an approximately 100-fold or 1000-fold reduction of required MR data compared with known image-based motion determination methods. One static reference image at, for instance, a certain phase of a deformation cycle of the object is sufficient to derive the whole dynamics of the object. This static reference MR image can be acquired during, for instance, one short breath hold, especially if the object is the abdomen or an organ in the abdomen region, or with a gated diastolic acquisition, if the object is the heart. The resulting non-linear least-squares problem in accordance with equations (1) and (12) can be solved by, for instance, Newton-type minimization algorithms, wherein the output of this algorithm is the adapted motion model or transform function u.

The above described motion determination procedure is preferentially adapted to directly target the motion model being in above described examples an anatomic transformation which can be non-linear, without requiring that for each acquisition time a respective MR image is reconstructed. The motion determination procedure can be adapted, for instance, to determine the motion with about 50 three-dimensional frames per second, wherein any periodic or non-periodic motion may be tracked. This motion tracking may not require any gating. However, if the motion to be determined is a periodic motion, the reference image might represent a certain phase of a periodic motion and may have been determined by using gating technology. Since the motion determination is not based on image registration, there is no need for anatomic contrast at each acquisition time as movement is entangled in preferentially a time-domain signal. Moreover, based on the preferred time-domain reconstruction a flexible design of the trajectory in the k-space is possible.

Although in above described embodiments the trajectory in the k-space for acquiring the k-space data at a respective acquisition time is spiral-like, the trajectory can also have another shape. For instance, the trajectory can be cartesian, echo planar (EPI) or radial. Although in above described embodiments the motion determination is adapted for determining the motion of, for instance, the heart or the pancreas, in other embodiments the motion determination can be adapted to determining the motion of other objects like other organs or technical objects.

Although in above described embodiments certain functions are used for describing the motion model, in other embodiments the motion model can be represented, particularly parameterized, in another way. Moreover, although in above described embodiments a certain non-image MR data function has been described, in other embodiments another non-image MR data function can be used which describes non-image MR data for different acquisition times depending on an MR image and depending on the motion model.

Other variations to the disclosed embodiments can be understood and effected by those skilled in the art in practicing the claimed invention, from a study of the drawings, the disclosure, and the appended claims In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Operations like the determination of the motion of the object performed by one or several units or devices can be performed by any other number of units or devices. These operations and/or the control of the motion determination device in accordance with the motion determination method and/or the control of the MR therapy system in accordance with the MR therapy method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a motion determination device for determining the motion of an object. The motion determination device comprises an MR information providing unit for providing an MR image of the object and for providing non-image MR data of the object which have been acquired at different acquisition times, and a motion determination unit for determining a motion field, which describes the motion of the object, depending on the provided non-image MR data acquired at the different acquisition times and the provided MR image. Since the non-image MR data, which are preferentially k-space data, are directly used for determining the motion field, i.e. without an intermediate reconstruction of MR images based on the non-image MR data, the motion field can be determined with a very high temporal resolution.

The invention claimed is:

1. A motion determination device for determining the motion of an object, the motion determination device comprising:
a magnetic resonance (MR) information providing unit for providing an MR image of the object and for providing non-image MR data of the object wherein the non-image MR data have been acquired at different acquisition times and are first k-space data, and a motion determination unit configured to determine a motion field, which describes the motion of the object, depending on the provided non-image MR data acquired at the different acquisition times and the provided MR image, wherein the motion determination unit is adapted to use the non-image MR data for determining the motion field.

2. The motion determination device of claim 1, wherein the motion determination device further comprises a dynamic MR image generating unit for generating a dynamic MR image of the object based on the provided MR image and the determined motion field, wherein the dynamic MR image of the object can be regarded as a sequence of different static MR images for different times, wherein the sequence of static MR images shows the motion of the object during a time period covered by the different times.

3. The motion determination device of claim 1, wherein the MR information providing unit is configured to provide a steady-state magnetization MR image as the MR image and/or to provide steady-state magnetization non-image MR data as the non-image MR data.

4. The motion determination device of claim 1, wherein the provided MR image is generated from second k-space data, wherein the first k-space data do not completely fill the k-space as the non-image MR data such that the first k-space data are undersampled as compared to the second k-space data which have been used for generating the provided MR image.

5. The motion determination device of claim 4, wherein the MR information providing unit is configured to provide the first k-space data such that they fill less than 5 percent of the k-space.

6. The motion determination device of claim 5, wherein the MR information providing unit is configured to provide the first k-space data such that they form a spiral-like trajectory in the k-space.

7. The motion determination device as defined in claim 1, wherein the motion determination device further comprises:
a motion model providing unit for providing a motion model which models the motion field, and
a non-image MR data function providing unit for providing a non-image MR data function describing non-image MR data for different acquisition times depending on an MR image and depending on the provided motion model,
wherein the motion determination unit is configured to determine the motion field by adapting the motion model such that the non-image MR data function yields the provided non-image MR data acquired at the different acquisition times given the provided MR image.

8. The motion determination device as defined in claim 7, wherein the non-image MR data function providing unit is configured to provide the non-image MR data function in accordance with $$s^j(k) = \int_{R^3} q(r) \exp(i 2\pi k \cdot u^j(r)) dr,$$

wherein $s^j$ denotes the non-image MR data for an acquisition time indicated by the index j, q(r) denotes MR image values of the provided reference MR image at different spatial positions r, k denotes the gradient trajectory in the k-space and $u^j(r)$ denotes the motion model defining a spatial position of a part of the object, which is indicated by the respective spatial position r, at the acquisition time indicated by the index j.

9. A magnetic resonance (MR) therapy system for treating an object being a living being or a part of a living being, the MR therapy system comprising:
a motion determination device for determining a motion of the object as defined in claim 1, and
a treating device for treating the object depending on the determined motion.

10. The MR therapy system of claim 9, wherein the treating device is configured to emit treating energy in the direction of the object under consideration of the determined motion.

11. A motion determination method for determining the motion of an object, the motion determination method comprising:
providing, by a magnetic resonance (MR) providing unit, an MR image of the object;
providing, by the MR information providing unit, non-image MR data of the object, wherein the non-image MR data have been acquired at different acquisition times and are first k-space data; and
determining a motion field, which describes the motion of the object, depending on the provided non-image MR data acquired at the different acquisition times and depending on the provided MR image by a motion determination unit wherein the non-image MR data are used for determining the motion field.

12. An MR therapy method for treating an object being a living being or a part of a living being, the MR therapy method comprising:
determining a motion of the object as defined in claim 11, and
treating the object depending on the determined motion by using a treating device.

13. A non-transitory computer readable medium configured to store a computer program for controlling: a motion determination device-, a magnetic resonance (MR) information providing unit for providing an MR image of an object and for providing non-image MR data of the object wherein the non-image MR data have been acquired at different acquisition times and are first k-space data, wherein the motion determination device includes a motion determination unit configured to determine a motion field, which describes the motion of the object, depending on the provided non-image MR data acquired at the different acquisition times and the provided MR image, wherein the motion determination unit is adapted to use the non-image MR data for determining the motion field, wherein the computer program comprises machine executable instructions for causing the motion determination device to carry out the motion determination method of claim 11 when the computer program is run on a controller controlling the motion determination device.

14. A non-transitory computer readable medium configured to store a computer program for controlling a magnetic resonance (MR) therapy system, wherein the MR therapy system includes: (a) a motion determination device for determining the motion of an object, the motion determination device comprising an MR information providing unit for providing an MR image of an object and for providing non-image MR data of the object wherein the non-image MR data have been acquired at different acquisition times and are k-space data, and further comprising a motion determination device includes a motion determination unit configured to determine a motion field, which describes the motion of the object, depending on the provided non-image MR data acquired at the different acquisition times and the provided MR image, wherein the motion determination unit is adapted to use the non-image MR data for determining the motion field; and (b) a treating device for treating the object depending on the determined motion, wherein the computer program comprises machine executable instructions for causing the MR therapy system to carry out the MR therapy method of claim 12 when the computer program is run on a controller controlling the MR therapy system.

15. The method of claim 11, wherein the provided MR image is generated from second k-space data, wherein the first k-space data do not completely fill the k-space as the non-image MR data such that the first k-space data are undersampled as compared to the second k-space data which have been used for generating the provided MR image.

16. The method of claim 15, wherein the first k-space data fill less than 5 percent of the k-space.

17. The method of claim 16, wherein the first k-space data form a spiral-like trajectory in the k-space.

18. The non-transitory computer readable medium of claim 13, wherein the provided MR image is generated from second k-space data, wherein the first k-space data do not completely fill the k-space as the non-image MR data such that the first k-space data are undersampled as compared to the second k-space data which have been used for generating the provided MR image.

19. The non-transitory computer readable medium of claim 18, wherein the first k-space data fill less than 5 percent of the k-space.

20. The non-transitory computer readable medium of claim 19, wherein the first k-space data form a spiral-like trajectory in the k-space.

\* \* \* \* \*